United States Patent [19]

Lee et al.

[11] Patent Number: 4,739,114

[45] Date of Patent: Apr. 19, 1988

[54] PROCESS FOR THE PREPARATION OF 3-ALKYL-SUBSTITUTED GLUTARIC ACIDS AND 2-ALKYL-SUBSTITUTED SUCCINIC ACIDS

[75] Inventors: Young J. Lee; Robert C. Ligon; Herbert E. Johnson, all of Raleigh, N.C.

[73] Assignee: Rhone-Poulenc Agrochimie, Lyon, France

[21] Appl. No.: 430,365

[22] Filed: Sep. 30, 1982

[51] Int. Cl.$^4$ .................... C07C 51/245; C07C 55/02
[52] U.S. Cl. ................................. 562/524; 562/528; 562/590; 562/593; 568/346
[58] Field of Search ........................... 562/524, 528

[56] References Cited

U.S. PATENT DOCUMENTS

| 2,005,183 | 6/1935 | Flemming et al. | 562/528 |
| 2,299,013 | 10/1942 | Flemming et al. | 562/528 |
| 2,920,087 | 1/1960 | Hoy | 562/528 |
| 4,018,827 | 4/1977 | Rao et al. | 562/528 |
| 4,340,753 | 7/1982 | Cella | 562/528 |

OTHER PUBLICATIONS

March, Jerry, *Advanced Organic Chemistry, Second Edition*, New York: McGraw-Hill Book Company, 1977, pp. 1089–1090.
Wagner et al, *Synthetic Organic Chemistry*, New York: John Wiley & Sons, Inc., 1953, p. 420.
R. H. Young, Chem. Comm., 704 (1970).
Beutel, J. Am. Chem. Soc., vol. 93, p. 2615 (1971).

*Primary Examiner*—Vivian Garner
*Attorney, Agent, or Firm*—Morgan & Finnegan

[57] ABSTRACT

This invention relates to a novel method of preparing 3-alkyl-substituted glutaric acids and 2-alkyl-substituted succinic acids from 5-alkyl substituted 1,3-cyclohexanediones or 3-alkyl-substituted-5-ketohexanoic acids via transition-metal catalyzed oxidation.

16 Claims, No Drawings

PROCESS FOR THE PREPARATION OF 3-ALKYL-SUBSTITUTED GLUTARIC ACIDS AND 2-ALKYL-SUBSTITUTED SUCCINIC ACIDS

FIELD OF THE INVENTION

This invention relates to a novel method of preparing 3-alkyl-substituted glutaric acids and 2-alkylsubstituted succinic acids from 5-alkyl-substituted 1,3-cyclohexanediones or 3-alkyl-substituted-5-ketohexanoic acids via transition-metal catalyzed oxidation.

BACKGROUND OF THE INVENTION

Certain 2-aryl-1,3-cyclohexanediones and their esters are known to be extremely active, biological compounds. U.S. Pat. Nos. 4,175,135 and 4,256,657 and copending application U.S. Ser. No. 781,781 filed Mar. 28, 1977, U.S. Pat. No. 4,422,870 all of which are herein incorporated by reference, teach the usefulness of these compounds as herbicidal and miticidal agents and as agents for orally controlling acarina ectoparasites on warm blooded animals.

3-Alkyl-substituted glutaric acids are important intermediates in the manufacture of the 2-aryl-1,3-cyclohexanediones.

A number of synthetic routes for the preparation of the 3-alkyl-substituted glutaric acids; specifically the 3,3-dimethyl-glutaric acid have been described in the prior art.

The Guareschi synthesis involves an initial reaction of ethyl cyanoacetate with acetone to give dicyanoglutarimide which upon subsequent hydrolysis with dilute sulfuric acid gives 3,3-dimethyl-glutaric acid in an 55–60% yield. This process, however, uses ethyl cyanoacetate, a relatively expensive chemical; generates large quantities of ammonium sulfate; and requires long reaction times.

A second method involves the oxidation of 5,5-dimethyl-1,3-cyclohexanedione with sodium hypochlorite to produce the 3,3-dimethyl-glutaric acid. Although good yields can be realized via this method, it suffers the major disadvantages relating to the disposal of the chloroform and the copious quantities of inorganic salts generated by the reaction.

A third method uses relatively inexpensive isophorone as a starting material; generates 3,3-dimethyl-5-ketohexanoic acid from the isophorone by ozonolysis; and oxidizes the acid with sodium hypochlorite to produce the 3,3-dimethyl-glutaric acid. This method also suffers from the disposal problems attendant with the afore-described second method.

The prior art has also disclosed two processes for the oxidation of 5,5-dimethyl-1,3-cyclohexanedione.

R. H. Young, Chem. Comm; 704 (1970) reported that the photo-oxidation of 5,5-dimethyl-1,3-cyclohexanedione yielded 3,3-dimethyl-glutaric acid and Beutel, J. Am. Chem. Soc. Vol. 93, pg 2615 (1971) reported that the primary product of a radical initiator catalyzed reaction of 5,5-dimethyl-1,3-cyclohexanedione and oxygen was "a thermally unstable species which was found to decompose to 3,3-dimethyl-glutaric acid". Neither the Young nor the Beutel reaction methods are desirable for commercial operations.

SUMMARY OF THE INVENTION

In accordance with the present invention, it has been discovered that 5-alkyl-substituted-1,3-cyclohexanedione and 3-alkyl-substituted-5-ketohexanoic acid compounds can be oxidized with air in an acid medium in the presence of a transition-metal catalyst to give 3,3-alkyl-substituted glutaric acid in high yields.

DETAILED DESCRIPTION OF THE INVENTION

The invention relates to the discovery that 3,3-alkyl-substituted glutaric acid can be prepared in yields of up to about 75% from the air (oxygen) oxidation of either a 5-alkyl-substituted-1,3-cyclohexanedione or a 3-alkyl-substituted-5-ketohexanoic acid in an acid medium in the presence of a transition-metal catalyst. Preferably, a promotor and an initiator are also present.

Major by-products of the reaction of the invention are the 2-alkyl-substituted succinic acids.

The 5-alkyl-1,3-cyclohexanedione starting material can be conveniently made from the reaction of diethyl malonate with a compound of the formula $(R)_n C=CHC(O)CH_3$ wherein R is hydrogen or an alkyl group having from 1 to 5 carbon atoms and n is 1 or 2. The reaction is preferably carried out in the presence of sodium ethoxide.

The 3-alkyl substituted-5-ketohexanoic acid starting material is readily prepared from the ozonolysis of a compound of the formula

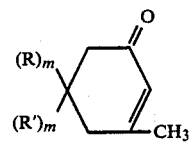

wherein R is as described above and m can be 0 or 1 or by base-catalyzed oxidation with hydrogen peroxide.

The concentration of the starting materials is preferably in the range of from about 5 to about 30% by weight of acid solvent.

The transition metals which have been found to be effective catalysts in the reaction of the invention are the heavy metals with the preferred being selected from the group consisting of manganese, cobalt, silver, nickel, thallium, vanadium, copper, lanthanum, and combinations thereof. The most preferred metal catalyst is selected from the group consisting of manganese, cobalt, silver, nickel, thallium, and combinations thereof.

When it is desired to maximize the yield of the 2-alkyl-substituted succinic acids, the most preferred metal catalyst is selected from the group consisting of vanadium, copper, lanthanum and combinations thereof.

The catalysts are readily available commercially in the form of metal salts such as the acetates, halides and carbonates. The preferred salt is one that shares the anion with that of the reaction medium.

The catalysts are used at a concentration in the range of from about 0.05 to about 5% by weight based on the weight of the acid solvent with from about 0.2 to about 2% preferred.

A co-catalyst selected from the effective metals can be added to increase the activity which increases the rate of oxidation. The concentration of the co-catalyst can vary from about 0.2 to about 1.0 times the weight of the primary catalyst.

The metal catalysts used in this invention can be recycled, thus substantially reducing catalyst and toxic metal discharge to the environment.

Any organic acid that is liquid at the reaction temperatures and pressures can serve as the solvent medium. The preferred solvent is acetic acid since it is resistant to further oxidation. The oxidation reaction of this invention can be carried out in aqueous acetic acid. It is preferred that the amount of water in the acid medium should not exceed about 20 volume percent although the oxidation may tolerate higher concentrations of water. It is most preferred that the water concentration in the final oxidation stage be below about 10%.

Gaseous oxygen as either pure molecular oxygen, air or an oxygen-containing gas is used as the oxidant. The gaseous oxygen to the reactant ratio in the acid solvent should be high enough to avoid a reaction mixture that is oxygen starved but should not be sufficiently high as to create an unnecessary safety hazard from excessive oxygen break-through by forming an explosive mixture of oxygen, solvent acid and hydrocarbon. To be at safe levels, the oxygen concentrations in the off-gas must be no more than 8%.

The gaseous oxidant and the reactant in the liquid medium can be reacted in a closed batch system with sufficient oxygen and reaction time provided to achieve the desired conversion. The reaction time in a batch mode of operation may be varied from about 1 to about 24 hours. The oxidation can also be carried out in a semi-batch mode by bubbling oxygen through the liquid reaction medium or in a continuous mode.

Any substance affording bromine, the bromide being in elemental, ionic, organic or inorganic form, is useful as a promoter. Preferably, the bromine may be provided in the form of hydrobromic acid, sodium bromide, potassium bromide, metal bromide, or tetrabromoethane. The most preferred promoter is aqueous hydrobromic acid. The concentration of the promoter should exceed 1.5 parts by weight of the weight of the metal catalyst.

In a preferred embodiment, a chain initiator is added to shorten the induction period and increase the rate of formation of the desired product. Any initiator that yields free radicals on thermal decomposition will suffice; the preferred initiators being peroxides such as dibenzoyl peroxide and t-butyl peroxide. The most preferred initiator being t-butyl peroxide. The concentration of the initiator should be from about 0.01 to about 1 percent by weight based on the starting material with the preferred concentration being from about 0.05 to about 0.2 percent. Addition of an initiator may not be necessary in a continuous process.

The temperature range of the process is from about 25 to about 200° C.; about 80 to about 120° C. being the preferred range.

The pressure of the system should be sufficient to maintain liquid phase at the reaction temperature. Although the process may be operated at any pressure from about atmospheric to about 500 psig.; about 100 to about 200 psig is preferred.

Higher temperatures and pressures exceeding 500 psig are avoided to minimize product degradation and decomposition of acid solvent.

It is desirable that the reaction vessel provide good gas-liquid contact in a well-mixed liquid. Mixing is preferably accomplished by mechanical means or by gas-spargers.

Preferably, the reaction vessel is constructed of corrosion resistant metals such as titanium and tantalum or other corrosion resistant materials such as glass and porcelain to minimize corrosion problems which can affect catalyst performance.

The following examples are set forth for purposes of illustration so that those skilled in the art may better understand the invention, and it should be understood that they are not to be construed or limiting this inventors in any manner.

EXAMPLE 1

Preparation of 5,5-Dimethyl-1,3-Cyclohexanedione

In a dry 2-L, three-necked, round-bottomed flask, fitted with a liquid-sealed stirrer, a 500-cc. dropping funnel, and an efficient reflux condenser protected at the top with a calcium chloride tube, is placed 400 cc. of absolute alcohol. Through the condenser tube is added 23 g. (1 gram atom) of clean sodium at such a rate that the solution is kept at the boiling temperature. After the sodium has dissolved completely, 170 g. (1.06 moles) of ethyl malonate is added, and then 100 g. (1.02 mmoles) of freshly distilled mesityl oxide is added slowly through the dropping funnel. The solution is refluxed with constant stirring for two hours, after which a solution of 125 g. (2.2 moles) of potassium hydroxide in 575 cc. of water is added and the mixture is stirred and refluxed again on the water bath for six hours.

The mixture while still hot is made just acid to litmus with dilute hydrochloric acid (1 volume concentrated acid to 2 volumes water; sp. gr. 1.055); about 550 cc. is required. The flask is fitted with a condenser set for distillation, and as much alcohol as possible (about 550 cc.) is distilled by heating on a water bath.

The residue in the flask is boiled with about 15 g. activated charcoal filtered, and the treatment with the decolorizing charcoal repeated. The residue is again neutralized to litmus with dilute hydrochloric acid (about 150 cc.) and again boiled with charcoal. The hot, neutral or alkaline, yellow filtrate is finally made distinctly acid to methyl orange with additional dilute hydrochloric acid (50 to 100 cc.), boiled for a few minutes, and allowed to cool, whereupon the methone crystallizes. The product is filtered by suction from the acid liquid, washed with ice-cold water, and dried in the air. The yield is 96–122 g. (67–85 percent of the theoretical amount).

EXAMPLE 2

Preparation of 3,3-Dimethyl-5-Ketohexanoic Acid

Isophorone (138 g) and 30% hydrogen peroxide (730 g) are dissolved in isopropanol (500 ml), and the solution is cooled to 15° C. 3N Sodium hydroxide solution (800 ml) is added slowly over a three-hour period to maintain the temperature of the reaction below 20° C. by adjusting the addition rate of sodium hydroxide solution and cooling with an ice-water bath. The reaction is allowed to warm to ambient temperature while stirring for 16 hours. The reaction mixture is extracted once with isopropyl ether (200 ml) then treated with sodium bisulfite (40 g) and acidified to pH 2 with concentrated hydrochloric acid (225 ml). The solution is extracted twice with methylene chloride (200 ml) and the resulting methylene chloride solution stripped under vacuum at 40° C., 10 mm Hg to give 3,3-dimethyl-5-ketohexanoic acid as a residue product.

EXAMPLE 3

Preparation of 5-Isopropyl-1,3-Cyclohexanedione

To a fresh solution of sodium ethoxide prepared from 23 g (1.0 mole) of sodium and 700 ml of absolute ethanol is added 168.2 g (1.05 mole) of diethyl malonate and 114.24 g (1.02 mole) of distilled 5-methyl-3-hexene-2-one. The mixture is refluxed for 1 hour; an additional 125 ml of ethanol added; and refluxing continued for two more hours. A solution of 123.4 g of potassium hydroxide in a 600 ml of water is then added and the reaction mixture refluxed for 6 hours. The mixture is then neutralized with 12% hydrochloric acid to pH 4. The ethanol is distilled and the mixture treated with three 15 g portions of activated charcoal. The hot reaction mixture is filtered through filter aid after acidification to pH 2. The product is extracted with hot isopropyl ether (700 ml). Cooling of the isopropyl ether layer results in 60.5 g (40% yield) of the product, m.p. 52°–65° C.

EXAMPLES 4–28

Oxidations of 5,5-dimethyl-1,3-cyclohexanedione (Ex. 4–11); 3,3-dimethyl-5-ketohexanoic acid (Ex. 12–22); and 5-isopropyl-1,3-cyclohexanedione (Ex. 23–28) are carried out to produce 3,3-dimethyl glutaric acid (Ex. 4–22) and 3-isopropyl glutaric acid (Ex. 23–28) under various conditions according to the following general procedures of this invention:

A mixture of starting material, catalyst, promoter, and initiator in acetic acid is placed in a 2-liter autoclave. The reactor is pressurized to the desired pressure with air/oxygen. The reactor is then slowly heated to the operating temperature with rocking (agitation) and held at the operating temperature for a predetermined time. The autoclave is cooled to room temperature and then depressurized by venting the gas slowly. The product is isolated by extracting the reaction mixture with ether. The crude product can br further purified by recrystallizing from a suitable solvent.

The starting materials, reaction conditions, and results are summarized in Tables I through III.

TABLE I

Oxidation of 5,5-Dimethyl-1,3-Cyclohexanedione

| Starting Material (g) | AcOH[1] (ml) | Co(OAc)$_2$ 4H$_2$O (g) | Mn(OAc)$_2$[2] 4H$_2$O (g) | HBr (48%) (g) | t-Butyl Peroxide (g) | Temp (°C.) | Pressure (psig) | Oxidant | Rxn Time (hr) | Crude Product (g) |
|---|---|---|---|---|---|---|---|---|---|---|
| 7.01 | 50 + 5 H$_2$O | 0.2 | — | — | 0.2 | 100 | 200 | Air | 1 | 5.65 |
| 7.01 | 50 | 0.1 | 0.1 | 0.2 | 0.2 | 100 | 200 | Air | 2 | 7.4 |
| 14.0 | 50 | 0.1 | 0.1 | 0.2 | 0.2 | 100 | 100 | O$_2$ | 3 | 14.57 |
| 14.0 | 50 | 0.1 | 0.1 | 0.2 | 0.2 | 130 | 100 | O$_2$ | 3 | 14.0 |
| 7.01 | 50 | 0.1 | 0.1 | 0.2 | 0.2 | 70 | 200 | Air | 6 | 6.91 |
| 7.01 | 50 | 0.1 | 0.1 | 0.2 | 0.2 | 100 | 200 | Air | 1 | 6.91 |
| 7.01 | 50 | 0.1 | 0.1 | 0.2 | — | 100 | 200 | Air | 3 | 7.1 |
| 7.01 | 100 | 0.1 | 0.1 | 0.2 | 0.2 | 100 | Atm. | O$_2$ | 15 | 7.31 |

[1] acetic acid
[2] cobalt acetate

TABLE II

Oxidation of 3,3-Dimethyl-5-Ketohexanoic Acid

| Starting Material (g) | AcOH (ml) | Co(OAc)$_2$ 4H$_2$O (g) | Mn(OAc)$_2$ 4H$_2$O (g) | Other Catalysts | HBr (48%) (g) | t-Butyl Peroxide (g) | Temp (°C.) | Pressure (psig) | Oxidant | Rxn Time (hr) | Crude Product (g) |
|---|---|---|---|---|---|---|---|---|---|---|---|
| 7.91 | 50 | 0.1 | 0.1 | — | 0.2 | 0.2 | 100 | 100 | O$_2$ | 3 | 5.85 |
| 7.91 | 50 | 0.1 | 0.1 | — | 0.2 | 0.2 | 100 | 200 | Air | 3 | 6.2 |
| 7.91 | 50 | — | 0.1 | — | — | — | 100 | 200 | Air | 3 | 6.21 |
| 7.90 | 100 | 0.25 | 0.25 |  | 0.3 | 0.2 | 150 | 200 | O$_2$ | 2 | 4.61 |
| 7.90 | 100 | 0.25 | 0.25 | 0.1 Ag$_2$O | 0.2 | 0.2 | 125 | 100 | O$_2$ | 2 | 6.09 |
| 7.90 | 100 | — | 0.25 | 0.1 Ag$_2$O | 0.2 | 0.2 | 150 | 200 | O$_2$ | 2 | 5.41 |
| 7.9 | 100 | — | 0.25 | — | 0.2 | 0.2 | 125 | 100 | O$_2$ | 2 | 5.45 |
| 7.9 | 100 | — | 0.25 | — | 0.2 | 0.2 | 175 | 200 | O$_2$ | 2 | 4.30 |
| 15.8 | 100 | — | 0.25 | 0.1 Ag$_2$O | 0.2 | 0.2 | 175 | 200 | O$_2$ | 2 | 6.04 |
| 7.9 | 100 | 0.25 | 0.25 | 0.3 NiNO$_3$ | 0.1 | 0.2 | 150 | 100 | O$_2$ | 2 | 4.18 |
| 7.9 | 100 | 0.25 | 0.25 | 0.25 Tl(OAc) | 0.1 | 0.2 | 100 | 200 | O$_2$ | 2 | 4.53 |

TABLE III

Oxidation of 5-Isopropyl-1,3-Cyclohexanedione

| Starting Material (g) | AcOH (ml) | Co(OAc)$_2$ 4H$_2$O (g) | Mn(OAc)$_2$ 4H$_2$O (g) | HBr (48%) (g) | t-Butyl Peroxide (g) | Temp (°C.) | Pressure (psig) | Oxidant | Rxn Time (hr) | Crude Product (g) |
|---|---|---|---|---|---|---|---|---|---|---|
| 7.7 | 50 | 0.1 | 0.1 | 0.2 | 0.2 | 100 | 200 | Air | 3 | 7.6 |
| 7.7 | 50 | 0.1 | 0.1 | 0.2 | 0.2 | 100 | 100 | O$_2$ | 3 | 5.6 |
| 7.7 | 50 | 0.1 | 0.1 | 0.2 | 0.2 | 100 | 300 | O$_2$ | 1 | 6.7 |
| 7.7 | 50 | 0.1 | 0.1 | 0.2 | 0.2 | 80 | 300 | O$_2$ | 1 | 7.8 |
| 7.7 | 50 | 0.1 | 0.1 | 0.2 | 0.2 | 50 | 300 | O$_2$ | 1 | 8.0 |
| 8.7 | 50 | 0.1 | 0.1 | 0.2 | 0.2 | 100 | 200 | Air | 3 | 8.6 |

The following examples relate to the production of the by-product 2,2-dimethyl succinic acid.

EXAMPLES 29-31

In the following examples, a 2 L pressure bomb is charged with 3,3-dimethyl-5-ketonoic acid (7.90, 0.05 mole), the appropriate catalyst mixture (0.001 moles of each component), 48% aqueous HBr (0.2 g, 0.001 mole) and t-butyl peroxide (0.2 g, 0.0015 mole). The bomb is conditioned by pressurizing to 200 psi with $O_2$ and venting. The conditioning procedure is repeated and the bomb pressurized to 250 psi with $O_2$. The bomb is placed in a heated rocker assembly and heated to 150° C. for 2 hours while rocking. The bomb is cooled to ambient temperature, vented, and the contents washed into a bottle with acetone. The reaction mixture is stripped of solvent on a rotary evaporator, the residue dissolved in diethyl ether (100 ml.) and extracted twice with 10% aqueous hydrochloric acid (25 ml). The ether layer is dried over magnesium sulfate, filtered, and stripped on a rotary evaporator. The residue is analyzed by high pressure liquid chromatography.

Twenty combinations of four metal catalysts each are replicated four times. In the series, each metal catalyst is used four times. Table IV shows the mole ratio of the 2,2-dimethyl succinic acid, (DMSA) to the 3,3-dimethyl glutaric acid (DMGA) produced for each replicate.

TABLE IV

| | (DMSA/DMGA) MOLE RATIO FOR EACH METAL ION | | | |
|---|---|---|---|---|
| | Rep 1 | Rep 2 | Rep 3 | Rep 4 |
| Copper Cu(OAC)$_2$ H$_2$O | 5.92 | 4.39 | 3.26 | 2.59 |
| Lanthanum La$_2$O$_3$ | * | 5.21 | 5.92 | 3.26 |
| Vanadium Vo(OAc)$_2$ | 4.61 | 5.02 | 5.26 | 4.39 |

*Conversion less than 50%

We claim:

1. A method of preparing 3-alkyl-substituted glutaric acids and 2-alkyl-substituted succinic acids which comprises reacting a compound of Formula A

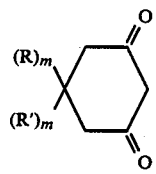

(A)

wherein R and R' are individually hydrogen or an alkyl group having from 1 to 5 carbon atoms, and m is 0 or 1, or Formula B

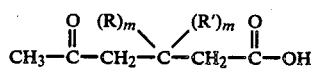

(B)

wherein R, R' and m are as described in Formula A, with an oxygen-containing gas in an acid medium in the presence of a heavy-metal catalyst wherein said heavy-metal is selected from manganese, cobalt, silver, nickel, thallium, vanadium, copper, lanthanum and combinations thereof.

2. A method of preparing 3-alkyl-substituted glutaric acids and 2-alkyl-substituted succinic acids which comprises reacting a compound of Formula A

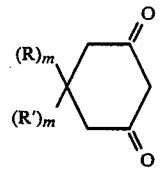

(A)

wherein R and R' are individually hydrogen or an alkyl group having from 1 to 5 carbon atoms, and m is 0 or 1, or Formula B

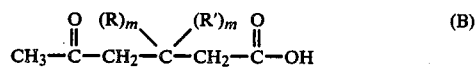

(B)

wherein R, R' and m are as described in Formula A, with an oxygen-containing gas in an acid medium in the presence of a heavy-metal catalyst wherein said heavy-metal is selected from manganese, cobalt, silver, nickel, thallium and combinations thereof.

3. A method of preparing 3-alkyl-substituted glutaric acids and 2-alkyl-substituted succinic acids which comprises reacting a compound of Formula A

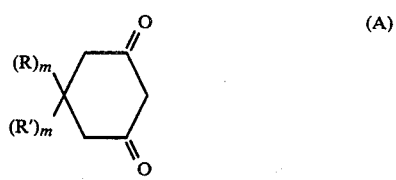

(A)

wherein R and R' are individually hydrogen or an alkyl group having from 1 to 5 carbon atoms, and m is 0 or 1, or Formula B

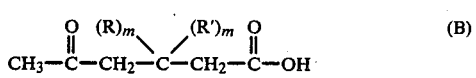

(B)

wherein R, R' and m are as described in Formula A, with an oxygen-containing gas in an acid medium in the presence of a heavy-metal catalyst wherein said heavy-metal catalyst is in the form of a salt.

4. A method of preparing 3-alkyl-substituted glutaric acids and 2-alkyl-substituted succinic acids which comprises reacting a compound of Formula A

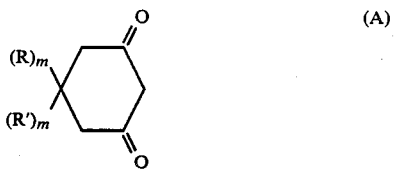

(A)

wherein R and R' are individually hydrogen or an alkyl group having from 1 to 5 carbon atoms, and m is 0 or 1, or Formula B

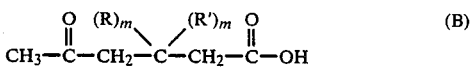

(B)

wherein R, R' and m are as described in Formula A, with an oxygen-containing gas in an acid medium in the presence of a heavy-metal catalyst salt wherein said heavy-metal catalyst salt anion is selected from the acetates, the halides and the carbonates.

5. A method of preparing 3-alkyl-substituted glutaric acids and 2-alkyl-substituted succinic acids which comprises reacting a compound of Formula A

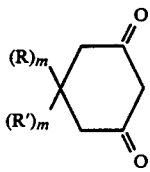

wherein R and R' are individually hydrogen or an alkyl group having from 1 to 5 carbon atoms, and m is 0 or 1, or Formula B

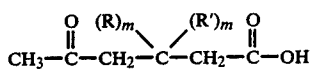

wherein R, R' and m are as described in Formula A, with an oxygen-containing gas in an acid medium in the presence of a heavy-metal catalyst salt wherein said heavy-metal catalyst salt anion is an acetate.

6. A method of preparing 3-alkyl-substituted glutaric acids and 2-alkyl-substituted succinic acids which comprises reacting a compound of Formula A

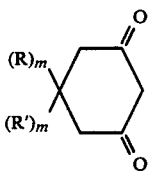

wherein R and R' are individually hydrogen or an alkyl group having from 1 to 5 carbon atoms, and m is 0 or 1, or Formula B

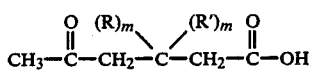

wherein R, R' and m are described in Formula A, with an oxygen-containing gas in an acid medium in the presence of a heavy-metal catalyst wherein said heavy-metal catalyst is present at a concentration of from about 0.2 to about 2% by weight based on the weight of acid medium.

7. A method of preparing 3-alkyl-substituted glutaric acids which comprises reacting a compound of Formula B

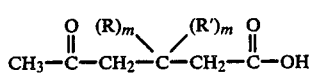

wherein R and R' are individually hydrogen or an alkyl group having from 1 to 5 carbon atoms, and m is 0 or 1, with an oxygen-containing gas in an acid medium in the presence of a heavy-metal catalyst wherein said heavy-metal is selected from manganese, cobalt, silver, nickel, thallium, vanadium, copper, lanthanum and combinations thereof.

8. A method of preparing 3-alkyl-substituted glutaric acids which comprises reacting a compound of Formula B

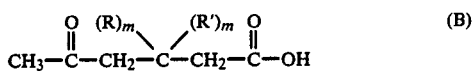

wherein R and R' are individually hydrogen or an alkyl group having from 1 to 5 carbon atoms, and m is 0 or 1, with an oxygen-containing gas in an acid medium in the presence of a heavy-metal catalyst wherein said heavy-metal is selected from manganese, cobalt, silver, nickel, thallium and combinations thereof.

9. A method of preparing 3-alkyl-substituted glutaric acids which comprises reacting a compound of Formula B

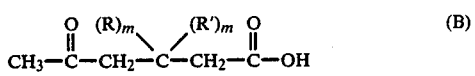

wherein R and R' are individually hydrogen or an alkyl group having from 1 to 5 carbon atoms, and m is 0 or 1, with an oxygen-containing gas in an acid medium in the presence of a heavy-metal catalyst wherein said heavy-metal catalyst is in the form of a salt.

10. A method of preparing 3-alkyl-substituted glutaric acids which comprises reacting a compound of Formula B

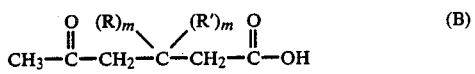

wherein R and R' are individually hydrogen or an alkyl group having from 1 to 5 carbon atoms, and m is 0 or 1, with an oxygen-containing gas in an acid medium in the presence of a heavy-metal catalyst salt wherein said heavy-metal catalyst salt anion is selected from the acetates, the halides and the carbonates.

11. A method of preparing 3-alkyl-substituted glutaric acids which comprises reacting a compound of Formula B

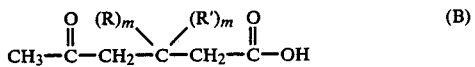

wherein R and R' are individually hydrogen or an alkyl group having from 1 to 5 carbon atoms, and m is 0 or 1, with an oxygen-containing gas in an acid medium in the presence of a heavy-metal catalyst salt wherein said heavy-metal catalyst salt anion is an acetate.

12. A method of preparing 3-alkylsubstituted glutaric acids which comprises:
reacting a compound of Formula A

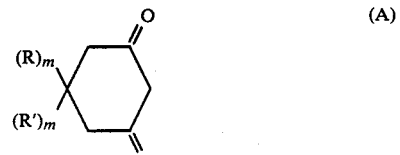

wherein R and R' are individually hydrogen or an alkyl group having from 1 to 5 carbon atoms, and m is 0 or 1, with air or oxygen in an organic acid; in the presence of a heavy-metal catalyst selected from the group consisting of the salts of manganese, cobalt, silver, nickel, thallium and combinations thereof;

a promoter selected from the group consisting of hydrobromic acid, sodium bromide, potassium bromide, metal bromide and tetrabomoethane; and a peroxide initiator.

13. The method of claim 12 wherein said organic acid is acetic acid.

14. The method of claim 13 wherein said peroxide initiator is t-butyl peroxide.

15. A method of preparing 3-alkyl-substituted glutaric acids which comprises:

reacting a compound of Formula B

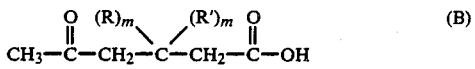

wherein R and R' are individually hydrogen or an alkyl group having from 1 to 5 carbon atoms, and m is 0 or 1, with air or oxygen in an organic acid, in the presence of a heavy-metal catalyst selected from the group consisting of the salts of manganese, cobalt, silver, nickel, thallium and combinations thereof;

a promoter selected from the group consisting of hydrobromic acid, sodium bromide, potassium bromide, metal bromide and tetrabromoethane; and a peroxide initiator.

16. The method of claim 15 wherein said organic acid is acetic acid.

* * * * *